(12) United States Patent
Khare

(10) Patent No.: US 6,855,359 B2
(45) Date of Patent: Feb. 15, 2005

(54) SOLUBLE ISOFLAVONE COMPOSITIONS

(75) Inventor: Anil B. Khare, Crystal, MN (US)

(73) Assignee: Cargill, Incorporated, Wayzata, MN (US)

( * ) Notice: Subject to any disclaimer, the term of this patent is extended or adjusted under 35 U.S.C. 154(b) by 0 days.

(21) Appl. No.: 10/714,542

(22) Filed: Nov. 14, 2003

(65) Prior Publication Data

US 2004/0137127 A1 Jul. 15, 2004

Related U.S. Application Data

(60) Provisional application No. 60/426,780, filed on Nov. 15, 2002, and provisional application No. 60/486,059, filed on Jul. 10, 2003.

(51) Int. Cl.$^7$ .............................. A23L 1/212; A23L 1/05
(52) U.S. Cl. ...................... 426/478; 426/479; 426/481; 426/590; 426/599; 426/615; 426/648
(58) Field of Search ................................ 426/590, 478, 426/479, 481, 599, 615, 648

(56) References Cited

U.S. PATENT DOCUMENTS

| | | |
|---|---|---|
| 4,264,466 A | 4/1981 | Carleton et al. |
| 4,742,066 A | 5/1988 | Deckner et al. |
| 5,141,611 A | 8/1992 | Ford |
| 5,702,752 A | 12/1997 | Gugger et al. |
| 5,792,503 A | 8/1998 | Gugger et al. |
| 5,821,361 A | 10/1998 | Waggle et al. |
| 5,925,684 A | 7/1999 | Schweikert et al. |
| 5,952,230 A | 9/1999 | Kim et al. |
| 6,033,714 A | 3/2000 | Gugger et al. |
| 6,096,343 A | 8/2000 | Gergely et al. |
| 6,132,795 A | 10/2000 | Holbrook et al. |
| 6,171,638 B1 | 1/2001 | Gugger et al. |
| 2002/0172724 A1 | 11/2002 | Forisz et al. |
| 2003/0108591 A1 * | 6/2003 | Meijer et al. ................ 424/439 |
| 2004/0023894 A1 | 2/2004 | Hasler-Nguyen et al. |

FOREIGN PATENT DOCUMENTS

| | | |
|---|---|---|
| WO | 96/10341 | 4/1996 |
| WO | 03/010116 | 2/2003 |

OTHER PUBLICATIONS

Merken and Beecher, "Measurement of Food Flavonoids by High–Performance Liquid Chromatography: A Review," *J. Agric. Food Chem.*, 2000, 48(3):577–599.

Murphy et al., "Isoflavones in Soy–Based Infant Formulas," *J. Agric. Food Chem.*, 1997, 45:4635–4638.

Song et al., "Soy isoflavone analysis: quality control and a new internal standard," *Am. J. Clin. Nutr.*, 1998, 68(suppl.),:1474S–1479S.

Wang and Murphy, "Isoflavone Content in Commercial Soybean Foods," *J. Agric. Food Chem.*, 1994, 42:1666–1673.

* cited by examiner

*Primary Examiner*—Helen Pratt
(74) *Attorney, Agent, or Firm*—Harry Gwinnell

(57) ABSTRACT

The present invention provides isoflavone compositions exhibiting improved solubility (e.g., light transmittance), taste, color, and texture characteristics, and methods for making the same. The isoflavone compositions are useful for incorporation in a variety of foodstuffs, beverages, dietary supplements, and pharmaceutical compositions allowing for improved taste, texture, color, and optical properties of the same.

16 Claims, No Drawings

SOLUBLE ISOFLAVONE COMPOSITIONS

CROSS REFERENCE TO RELATED APPLICATIONS

This application claims priority under 35 U.S.C. § 119(e) of U.S. Application No. 60/426,780, filed Nov. 15, 2002, and U.S. Application No. 60/486,059, filed Jul. 10, 2003.

TECHNICAL FIELD

The invention relates to isoflavone compositions, and more particularly, to isoflavone compositions with improved solubility (e.g., light transmittance), color, and taste, and methods for using such compositions to make beverages and foodstuffs.

BACKGROUND

Plants are a natural warehouse of bioactive compounds. A difficulty in accessing this abundant diversity of compounds lies in the separation of the various components. Isoflavones are an example of an interesting class of phenolic-containing plant flavonoid compounds that are believed to have a number of beneficial health effects on mammals. For example, isoflavones have been suggested to provide a beneficial effect on the symptoms experienced by meno-pausal and peri-menopausal women. Currently 15% of menopausal women are on Hormone Replacement Therapies (HRT) that employ animal estrogens. HRT products derived from animal estrogens are highly potent and activate all estrogen receptors. This potency is correlated with an increased risk of breast cancer and other complications. Since plant isoflavones have a lower affinity to the estrogen receptor, they may be preferred to animal estrogens for some uses. In addition, some research has indicated that isoflavones may even prevent or retard certain cancers, such as breast and prostate cancers, as well as have serum cholesterol-lowering effects.

Despite the beneficial effects associated with plant isoflavones, many individuals have not increased their intake of isoflavones, particularly those available from soy foods, because the variety of soy based foods in many countries have been limited and because many find the flavor and colors of soy foods bitter and unappetizing. In addition, earlier methods for isolating isoflavones often resulted in isoflavones compositions of reduced water solubility and thus limited applicability for incorporation into foodstuffs and beverages. Thus, it would be desirable to provide methods for isolating isoflavones from a variety of plant materials with improved purity, color, flavor, texture, and solubility to promote the incorporation of these beneficial nutrients in a variety of food, beverage, dietary supplement, and pharmaceutical products.

SUMMARY OF THE INVENTION

The present invention relates to methods for improving the aqueous solubility of isoflavone compounds isolated from plant materials such as soybean extracts. The invention also relates to compositions that contain isoflavones with improved solubility (e.g., light transmittance), color, flavor, and texture properties. The compositions of the present invention may be incorporated in a number of foodstuffs and beverages (e.g., juice beverages) with improved color, texture, light transmittance, and taste characteristics. Removing polyphenolic compounds from juice before adding isoflavone compositions of the invention helps to maintain the solubility of the isoflavones within the juice beverage.

Accordingly, in one aspect, the invention provide compositions having two or more isoflavones that represent about 15% to about 70% by weight of the composition. For example, the isoflavones can represent about 25% to about 65% by weight of the composition. Alternatively, in another embodiment, the isoflavones can represent about 35% to about 55% by weight of the composition.

The compositions of the present invention have about 0.5% to about 30%, by weight, of a hydrophilic polymer. Examples of hydrophilic polymers for use in the present invention include, without limitation, polyvinyl pyrrolidone (PVP), polyvinyl polypyrrolidone, (PVPP) polyvinyl formyl, polyvinyl alcohol, polypropylene glycol (PPG), polyvinyl caprolactam, polyethylene oxide, polyethylene glycol (PEG), or polyvinyl N-methylpyrrolidone. PEG and PVP are particularly useful hydrophilic polymers.

The compositions of the present invention exhibit, upon preparation of a mixture of about 0.03% by weight of the composition in water, a transmittance at 500 nm of at least 75% (e.g., at least 85% or 95%).

The compositions may be incorporated into a variety of foodstuffs. For example, the composition may be included in a beverage. The beverage may be a tea-based product, a fruit drink, or an energy drink. A beverage containing a composition of the present invention may exhibit a transmittance at 500 nm of at least 90%.

The present invention also relates to methods of making an isoflavone containing composition. In one embodiment, the method includes providing an organic plant extract containing two or more isoflavones and at least one organic solvent, and combining the organic plant extract with about 0.5% to 30% by weight of a hydrophilic polymer to produce a combined extract. The organic solvent in the combined extract is replaced with an aqueous solution to produce an aqueous extract. The aqueous extract is concentrated to produce the isoflavone composition. The isoflavone composition contains two or more isoflavones, with the isoflavones representing about 15% to about 70% by weight of the composition and exhibits, upon preparation of a mixture of about 0.03% by weight of the composition in water, a transmittance at 500 nm of at least 75%.

In another aspect the invention features a method of making an isoflavone composition. The method includes providing a starting composition that includes two or more isoflavones and combining the starting composition with a hydrophilic polymer to produce an isoflavone-polymer mixture. Either the starting composition or the hydrophilic polymer is in the aqueous phase. The isoflavone-polymer mixture may contain about 0.5% to about 30% by weight of the hydrophilic polymer. The isoflavone-polymer mixture is then heated and the isoflavone-polymer mixture is concentrated to produce the isoflavone composition. The isoflavone-polymer mixture may be heated to 100° C. (e.g., boiling).

Alternatively, the isoflavone composition can be made by combining a starting composition comprising two or more isoflavones with a hydrophilic polymer to produce an isoflavone-polymer mixture. The isoflavone-polymer mixture is suspended in an aqueous solution to result in a final concentration of from about 0.5 to about 30% by weight of the hydrophilic polymer. The aqueous isoflavone-polymer mixture is then heated and concentrated to produce the isoflavone composition. The isoflavone-polymer mixture may be heated to 100° C. (e.g., boiling).

Isoflavone compositions produced by the methods of the present invention contain two or more isoflavones, with the isoflavones representing about 15% to about 70% by weight of the composition. The isoflavone compositions further exhibit, upon preparation of a mixture of about 0.03% by weight of the composition in water, a transmittance at 500 nm of at least 75%.

The invention also features a method of making a juice beverage. The method includes combining a fruit juice with 0.15 to 3% by weight of PVP or PVPP to form a precipitate containing polyphenolic compounds; removing the precipitate from the fruit juice (e.g., by filtration or centrifugation); and adding at least 0.01% by weight of an isoflavone composition described above to the fruit juice to produce the beverage. The beverage exhibits a transmittance at 600 nm, that is increased at least 15% (e.g., at least 30% or 50%) relative to the transmittance of a corresponding beverage prepared without removing the polyphenolic compounds. The fruit juice can be apple, cranberry, orange, or grape juice concentrate. The increased transmittance of the beverage can be maintained upon storage of the beverage for at least 30 days at a temperature ranging from about 4° C. to about 25° C.

Juice beverages also can be made by combining a fruit juice with 0.15 to 3% by weight of PVP or PVPP and at least 0.01% by weight of an isoflavone composition described above to form a precipitate containing polyphenolic compounds endogenous to the fruit juice; and removing the precipitate from the fruit juice to produce the fruit beverage.

In another aspect, the invention features an isoflavone composition containing two or more isoflavones, where the isoflavones represent about 15% to about 70%, by weight, of the composition, and about 0.5% to about 30%, by weight, of a hydrophilic polymer, wherein the composition, upon preparation of a mixture of about 0.03% by weight of the composition in water, exhibits a transmittance at 500 nm of at least 75% and one or more excipients selected from the group consisting of buffers, stabilizers, diluents, sweeteners, flavorings, preservatives, and solubilizers. The invention also features a method of reducing symptoms of menopause in a woman. The method includes administering an amount of such a composition to the woman effective to reduce the symptoms of menopause.

The present invention also relates to methods of making an isoflavone containing composition. In one embodiment, the method includes providing an organic plant extract containing two or more isoflavones and at least one organic solvent, and combining the organic plant extract with about 0.5% to 30% by weight of a hydrophilic polymer to produce a combined extract. The organic solvent in the combined extract is replaced with an aqueous solution to produce an aqueous extract. The aqueous extract is concentrated to produce the isoflavone composition.

In another aspect the invention features a method of making an isoflavone composition. The method includes providing a starting composition that includes two or more isoflavones and combining the starting composition with a hydrophilic polymer to produce an isoflavone-polymer mixture. Either the starting composition or the hydrophilic polymer is in the aqueous phase. The isoflavone-polymer mixture may contain about 0.5% to about 30% by weight of the hydrophilic polymer. The isoflavone-polymer mixture is then heated and the isoflavone-polymer mixture is concentrated to produce the isoflavone composition. The isoflavone-polymer mixture may be heated to 100° C. (e.g., boiling).

Alternatively, the isoflavone composition can be made by combining a starting composition comprising two or more isoflavones with a hydrophilic polymer to produce an isoflavone-polymer mixture. The isoflavone-polymer mixture is suspended in an aqueous solution to result in a final concentration of from about 0.5 to about 30% by weight of the hydrophilic polymer. The aqueous isoflavone-polymer mixture is then heated and concentrated to produce the isoflavone composition. The isoflavone-polymer mixture may be heated to 100° C. (e.g., boiling).

Isoflavone compositions produced by the methods of the present invention contain two or more isoflavones, with the isoflavones representing about 15% to about 70% by weight of the composition. The isoflavone compositions further exhibit, upon preparation of a mixture of about 0.03% by weight of the composition in water, a transmittance at 500 nm of at least 75%.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the detailed description below. Other features, objects, and advantages of the invention will be apparent from the detailed description and from the claims.

DETAILED DESCRIPTION

In general, the invention provides isoflavone compositions exhibiting improved solubility, taste, color, and texture characteristics, and methods for making and using such isoflavone compositions. Isoflavones are phenolic compounds found in a variety of food sources including, in particular, soybeans and soy products. Isoflavones present in soy include both isoflavone aglycones and isoflavone glycosides, wherein a glucose molecule is attached via a glycosidic bond to the isoflavone backbone. Isoflavone aglycones present in soy include daidzein, genistein, and glycitein. The isoflavone glycoside compounds present in soy include: daidzin, genistin, glycitin, 6"-O-acetyldaidzin, 6"-O-acetylgenistin, 6"-O-acetylglycitin, 6"-O-malonyldaidzin, 6"-O-malonylgenistin, and 6"-O-malonylglycitin. The 6"-O acetyl and the 6"-O malonyl isoflavones are esterified derivatives of the glucose molecule at the 6 position. Approximately ninety-seven to ninety-eight percent of the naturally occurring isoflavones in soybeans are in the glycosylated form.

Isoflavones have the general structure shown below:

Isoflavone General Structure

TABLE 1

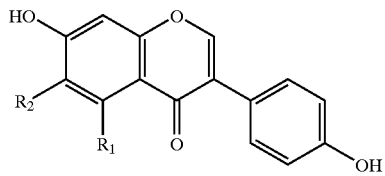

Aglycone Isoflavone General Structure

| Isoflavone | Formula | MW | $R_1$ | $R_2$ |
|---|---|---|---|---|
| Daidzein | $C_{15}H_{10}O_4$ | 254.24 | H | H |
| Genistein | $C_{15}H_{10}O_5$ | 270.24 | OH | H |
| Glycitein | $C_{16}H_{12}O_5$ | 284.26 | H | $OCH_3$ |

Glycosylated isoflavones can have the general structure shown below:

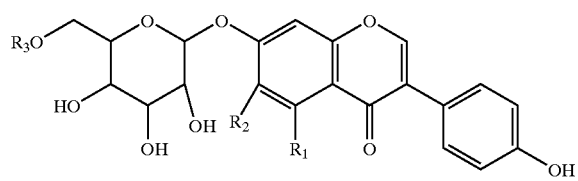

Glycosylated Isoflavone General Structures

| Isoflavone | $R_1$ | $R_2$ | $R_3$ |
|---|---|---|---|
| Daidzin | H | H | H |
| Genistin | OH | H | H |
| Glycitin | H | $OCH_3$ | H |
| Acetyldaidzen | H | H | $COCH_3$ |
| Acetylgenistin | OH | H | $COCH_3$ |
| Acetylglycitin | H | $OCH_3$ | $COCH_3$ |
| Malonyldaidzin | H | H | $COCH_2COOH$ |
| Malonylgenistin | OH | H | $COCH_2COOH$ |
| Malonylglycitin | H | $OCH_3$ | $COCH_2COOH$ |

For more information, see, generally, Merken and Beecher, *J. of Agricultural and Food Chemistry*, Vol. 48, No. 3, 2000.

Compositions of the invention contain two or more isoflavones, which represent between about 15 and 70% by weight of the composition. For example, the composition can contain between 20% to about 65%, 25% to about 60%, 35% to about 55%, or about 40% to 50%, by weight, isoflavones. Compositions of the invention also contain about 0.5% to about 30%, by weight, of a hydrophilic polymer. For example, about 2% to about 10% of a hydrophilic polymer can be added. The hydrophilic polymer can be any hydrophilic polymer that may be safely incorporated into a foodstuff. For example, the hydrophilic polymer may be approved as "Generally Recognized As Safe," or "GRAS," by the U.S. Food and Drug Administration (FDA). See, e.g., the EAFUS ("Everything" Added to Food in the United States) informational database maintained by the FDA Center for Food Safety and Applied Nutrition. Examples of hydrophilic polymers for use in the present invention include, without limitation, PVP, PVPP, polyvinyl formyl, polyvinyl alcohol, polypropylene glycol (PPG), polyvinyl caprolactam, polyethylene oxide, polyethylene glycol (PEG), or polyvinyl N-methyl pyrrolidone. The hydrophilic polymers can be present in a variety of average molecular weight (formula weight) ranges. For example, PEG 100, 200, 400, 600, or 1000 may be used or PPG 425 may be used. Alternatively, PVP of average molecular weight 10,000, 30,000, 40,000, or 55,000 may be used.

Isoflavone compositions, upon preparation of a mixture of about 0.03% by weight of the composition in water, exhibit a transmittance at 500 nm of at least 75% (e.g., at least 85% or 95%) at room temperature (typically 25° C.). Transmittance may be measured by standard techniques in the art. For example, an 0.03% by weight solution of a composition of the present invention (30 mg/100 ml water) may be prepared, followed by transfer of the solution to a UV/VIS spectrophotometer cell, and measurement of % transmittance on a UV/VIS spectrophotometer at 500 nm. The increased transmittance of the isoflavone compositions of the invention relative to commercially available isoflavone products is a reflection of the improved water solubility of the compositions.

Water solubility can be determined directly by the following procedure. At room temperature, 0.05 g of a sample is mixed with 50.0 g of deionized water in a 100-mL beaker. If the sample readily disperses, another 0.05 g of sample is added to the water and mixed. This process is repeated until the solubility limit has been exceeded. The mixture is stirred for 30 minutes, at which time insoluble material is removed by filtering the solution through a pre-weighed piece of filter paper. The filter paper containing the residue is placed in a weighed aluminum pan, and the sample is dried in a vacuum desiccator for 48 hours at room temperature. After drying, the pan containing the filter paper with insoluble material is weighed. The weight of water-soluble material and percent solubility is calculated.

Visually, the products of the present invention have a light tan to cream coloration compared to the redder appearance of the other commercially available products. Color is characterized by three distinct values, the L-value, a-value, and b-value. The L-value corresponds to brightness, with a higher value corresponding to a brighter product. The a-value assesses the red/green coloration with positive and negative values corresponding to the degree of red and green, respectively. Similarly, the b-value quantifies the degree of yellow/blue coloration with positive values relating to yellow hues and negative values to blue. The products of the present invention are significantly brighter, as indicated by its higher L-value, and have less red coloration (lower a-value). Isoflavone compositions of the present invention can have L-values greater than about 65 (e.g., greater than about 75, or between about 65 and 75) and can have a-values lower than about 4 (e.g., lower than about 2, or between 2 and 4).

Methods of Making Isoflavone Compositions

Isoflavone compositions can be prepared from a variety of plants including soybean, chick pea, red clover, subterranean clover, ground pea, milk vetch, marama bean, sword bean, jack bean, seaside sword bean, carao bean, cluster bean, balu, hyacinth bean, grass pea, Indian vetch, garden pea, djenko bean, goa bean, yam bean, broad bean, earth pea, lentil, jumping bean, alfalfa, velvet bean, African locust bean, inga, Cyprus vetch, yebnut, tallow tree, Polynesian chestnut, kudzu root, oil bean tree, mesquite, tamarind, fenugreek, Indian licorice, and ground nut, and from preparations of such plants and plant materials, such as defatted soy flakes, soy flour, soy germ flour, and soy meal. Soybeans, soy meal, soy flakes, soy flour, soy germ, soy germ flour, soy molasses (also known as soy solubles), Novasoy®, soy whey, and any other concentrated isoflavone product are particularly useful in the invention.

Isoflavone compositions of the invention can be prepared from solid (e.g., dried) or liquid materials (e.g., aqueous or organic extracts) that contain isoflavones. These materials are referred to a "starting compositions" or "starting extracts." In general, starting compositions or extracts are combined with a hydrophilic polymer and the resulting material is processed to obtain a composition of the invention.

Starting organic plant extracts may be prepared by methods described in the art. For example, a solid isoflavone product produced by conventional techniques can be resuspended in one or more organic solvents (e.g., 100% butanol) or an organic solution (e.g., a 94% butanol/water solution). In another embodiment, an aqueous suspension of an isoflavone product may be dried by conventional techniques and resuspended in an organic solution. In addition, the methods described in PCT Application PCT/US02/23555, filed Jul. 23, 2002, entitled "Process for Isolating Phenolic Compounds," can be used to prepare starting organic extracts. Briefly, the method of PCT/US02/23555 is described in Scheme I below:

Scheme I

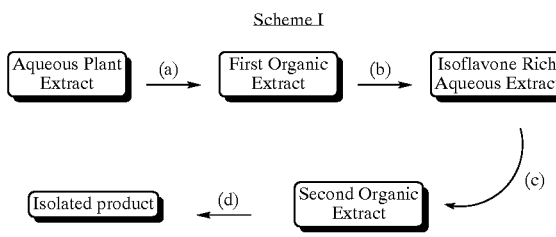

In the method of PCT/US02/23555, an aqueous alcohol plant extract is provided. Procedures for preparing aqueous alcohol plant extracts are known, and generally include extraction of the plant material in an aqueous alcohol, such as ethanol, at 60–80° C. After extracting, the alcohol is preferentially, but need not be, removed, resulting in a crude aqueous plant extract having an approximately neutral pH of about 6–8. See, for example, U.S. Pat. No. 6,132,795, which exemplifies conventional methods for preparing crude aqueous plant extracts containing isoflavones from plant materials. The aqueous plant extract can be pretreated at elevated pH to facilitate the subsequent organic extraction. In addition, the temperature of the pH-adjusted extract may be raised to a temperature above 40° C.

In step (a) of Scheme I, the pH of the aqueous plant extract may be adjusted to an approximately neutral pH ranging from about 6 to 8, and extracted with an immiscible organic solvent to yield a first crude organic extract. Useful organic solvents include 1-butanol, 2-butanol, t-butanol, pentanol, hexanol, heptanol, octanol, ethyl acetate, tetrahydrofuran, hexane, heptane, octane, isohexane, diethylether, methyl ethyl ketone, diisopropylether or other ethers, other polar or non-polar organic solvents that are immiscible with water, or mixtures of such solvents.

In step (b), the first organic extract is then itself extracted with an aqueous solution having a pH>10, preferably above 11, to yield an isoflavone rich aqueous extract. In step (c), the pH of the isoflavone rich aqueous extract is then adjusted to approximately neutral pH (pH 6–8) and extracted with organic solvent to yield a isoflavone rich second organic extract.

Alternatively, the aqueous plant extract may be treated as shown in Scheme II:

Scheme II

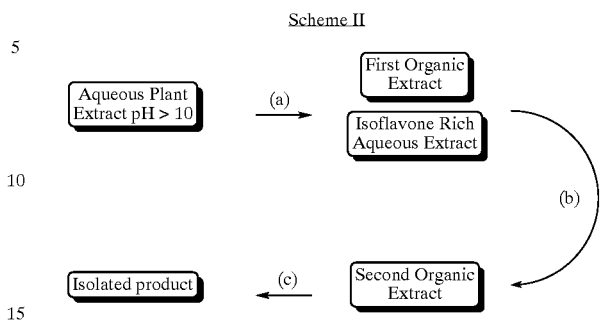

The pH of the starting aqueous plant extract can be elevated to greater than 10 and washed with an organic solvent as in step (a) from Scheme I to yield a first organic extract and an isoflavone rich aqueous extract. The resulting first organic extract contains impurities and is discarded. The isoflavone rich aqueous extract is then adjusted to an approximately neutral pH of 6–8 and extracted with an organic solvent as in step (c) from Scheme I to yield a second organic extract.

Compositions of the invention can be made using the second organic plant extract described above in either Scheme I or Scheme II. Alternatively, the second organic plant extract of Scheme I or Scheme II may be exposed to additional purification steps before processing according to the methods of the present invention. Additional purification procedures are well known and include ultrafiltration and adsorption chromatography. Additionally, purification further may include spray drying and re-crystallization of plant extracts. See, for example, U.S. Pat. Nos. 5,702,752; 5,792,503; 6,033,714; and 6,171,638. Materials resulting from the additional purifications can be resuspended in an organic solution before processing according to the methods of the present invention. For example, the material can be suspended in a butanol solution, e.g., a 94% butanol/water solution to result in a starting organic extract containing two or more isoflavones.

The starting organic extract is combined with a hydrophilic polymer to produce a combined extract. The hydrophilic polymer is provided at about 0.5% to about 30% by weight (final) of the combined extract. The hydrophilic polymer can be any hydrophilic polymer that may be safely incorporated into foodstuffs, dietary supplements, and beverages, as discussed above. The starting organic extract and hydrophilic polymer can be combined by methods well known in the art, including mixing, stirring, agitation, etc.

One or more organic solvents in the combined extract can be replaced with an aqueous solution to produce an aqueous extract. Methods for replacing the organic solvent in the combined extract are known in the art and include, for example, solvent exchange methods such as azeotropic distillation or evaporative techniques such as spray drying, rotary evaporation or tray drying, followed by resuspension in an aqueous solution. If the material is resuspended in an aqueous solution, the aqueous solution may be at an elevated temperature, or may be heated to an elevated temperature. For example, the aqueous solution may be at or heated above 50° C., 75° C., or 85° C. (e.g., to boiling (100° C.)).

The aqueous extract can be concentrated to produce an isoflavone composition of the invention. The concentration may be performed by methods known in the art. For example, the aqueous extract may be evaporated, rotoevaporated, spray dried, drum-dried, tray dried, or any combination thereof. While not being bound by any theory, it is believed that inclusion of the hydrophilic polymer in the isoflavone composition during formation of a solid isoflavone composition (e.g., during a spray-drying process) inhibits the improper packing of the isoflavone molecules, and promotes subsequent improved water solubility.

Alternatively, compositions of the invention can be produced from dried material or material in an aqueous phase. It is noted that "dried" material may contain residual levels of liquid. For example, with reference to Scheme I (described above), a starting composition can be obtained in step (d) by isolating the isoflavones from the isoflavone rich second organic extract by standard methods such as drying, chromatography, and crystallization, or any other well known method. For example, the second organic extract may be spray dried. Similar methods can be used to obtain a starting composition from Scheme II.

The starting composition is combined with a hydrophilic polymer to produce an isoflavone-polymer mixture. The hydrophilic polymer and starting composition may be combined by methods well known in the art, including mixing, stirring, agitation, etc. The hydrophilic polymer may be a solid or may be in the aqueous phase. For example, the starting composition can be in the aqueous phase and the hydrophilic polymer can be solid or the starting composition can be solid and the hydrophilic polymer can be in an aqueous phase. In some embodiments, both the starting composition and the hydrophilic polymer are in the aqueous phase. In other embodiments, both the starting composition and hydrophilic polymers are solids. In this case, the isoflavone-polymer mixture is suspended in an aqueous solution before proceeding.

The isoflavone-polymer mixture is then processed to produce an isoflavone composition of the invention. For example, the isoflavone-polymer mixture can be heated then concentrated as described above. The isoflavone-polymer mixture may be heated to above 50° C., 75° C., or 85° C. (e.g., to boiling (100° C.)).

Formulations of Isoflavone Compositions

Isoflavone compositions of the invention can be incorporated in a number of foodstuffs, dietary supplements, pharmaceutical composition, or beverages to impart improved color, texture, and light transmittance characteristics. Compositions of the invention are particularly useful for formulating clear beverages that exhibit reduced particulates and improved color and flavor profiles. Beverages (e.g., energy drinks, health drinks, fruit drinks, tea-based drinks) containing at least 0.03% by weight of a composition of the invention can have a transmittance at 500 nm of at least 90%.

To help maintain the solubility of the isoflavones when making juice beverages (e.g., apple, cranberry, orange, grapefruit, or grape juice beverages) or other beverages containing polyphenolic compounds (e.g., tea-based drinks), the polyphenolic compounds (e.g., anthocyanins) endogenous to the juice or other beverage can be removed before adding an isoflavone composition of the invention. Polyphenolic compounds endogenous to a fruit juice (e.g., a fruit juice concentrate) can be removed using PVP or PVPP. Fruit juice refers to the juice extracted directly from the fruit, with or without the use of processing aids. Fruit juice concentrate refers to fruit juice in which water has been removed in an amount sufficient to increase the Brix level to a value at least 50% over that of the fruit juice. Typically, a fruit juice or fruit juice concentrate is combined with 0.15 to 3% (e.g., 0.2, 0.5, 1, 1.5, 2, or 2.5%) by weight of PVP or PVPP and mixed to form a precipitate containing the polyphenolic compounds. For example, a fruit juice concentrate and PVP or PVPP can be combined, diluted with water to the desired Brix level of the juice, and mixed with or without the aid of a mechanical device. In some embodiments, the diluted mixture can be sonicated. Polyphenolic compounds within the juice bind to the PVP or PVPP, resulting in the formation of a precipitate. The precipitate can be removed by allowing it to settle (e.g., by gravity or by centrifugation) then decanting the supernatant. Alternatively, the precipitate can be removed by filtration.

After removing the precipitate, an isoflavone composition of the invention and other desired ingredients (e.g., flavorings, sweeteners, or vitamins) can be added to the fruit juice. For example, at least 0.01% by weight on an isoflavone composition can be added to the juice to produce a juice beverage. Such a beverage exhibits a transmittance at 600 nm that is increased at least 15% (e.g., at least 20, 25, 30, 35, 40, 45, 50, 55, 60, 65, or 75%) relative to the transmittance of a corresponding beverage prepared without removing the polyphenolic compounds. Transmittance can be measured as assessed above. The increased transmittance of juice beverages prepared in this manner is maintained upon storage (e.g., for 20, 30, 40 or more days) at temperatures ranging from about 4° C. to room temperature (about 25° C.). Color of juice beverages also can be assessed as described above.

In other embodiments, the polyphenolics can be removed by combining the fruit juice or juice concentrate with PVP or PVPP and an isoflavone composition then allowing a precipitate to form that contains the polyphenolic compounds endogenous to the fruit juice. The precipitate can be removed as discussed above.

In addition, the isoflavone compositions of the present invention may be incorporated into a variety of dietary supplements or pharmaceutical compositions (e.g., in the form of a liquid, solution, suspension, pill, capsule, tablet, gelcap, powder, gel, ointment, cream, nebulae, mist, atomized vapor, aerosol, phytosome, caplet, wafer, cookie, candy, energy bar, and the like). For example, an isoflavone composition can be formulated as a powdered mix that can be stirred into a beverage. Such dietary supplements or pharmaceutical compositions can be used for reducing or preventing symptoms experienced by menopausal and peri-menopausal women (e.g., hot flashes). Such dietary supplements or pharmaceutical compositions also can be used for treating diseases or conditions associated with decreased levels of estrogen in post-menopausal women (e.g., osteoporosis, cardiovascular disease, decreased cognitive function, urinary incontinence, or weight gain). As used herein, "treating" refers to preventing the development, delaying onset, slowing progression, or reducing severity of the disease or condition.

The amount of a dietary supplement or pharmaceutical composition effective for reducing or preventing symptoms experienced by menopausal and peri-menopausal women or diseases or conditions associated with decreased levels of estrogen in post-menopausal women is expected to vary in view of the variety of compositions that can be produced and the differing efficiencies of various routes of administration. For example, oral administration (e.g., in the form of a tablet, capsule, wafer, cookie, energy bar, or beverage) would be expected to require higher amounts than administration by intravenous injection. The amount of isoflavones in the supplement or composition can be adjusted using standard empirical routines for optimization, as is well understood in the art. In some embodiments, the supplements or compositions are formulated to provide about 0.01 mg to 1000 mg (e.g., 0.1 to 100, 1 to 1000, 2 to 800, 5 to 500, 5 to 50, 6 to 40, or 10 to 100 mg) of the isoflavones per administration.

Isoflavone compositions can be formulated as dietary supplements or pharmaceutical compositions by mixing with one or more excipients, including, for example, buffers, stabilizers (e.g., albumin), diluents, preservatives, flavoring, sweeteners, or solubilizers, and any other desired ingredients (e.g., vitamins). In some embodiments, the dietary supplements or pharmaceutical compositions are formulated to facilitate sustained release. Diluents can include water, saline, dextrose, ethanol, glycerol, and the like. Additives for isotonicity can include sodium chloride, dextrose, mannitol, sorbitol, and lactose. Pharmaceutical compositions can be formulated for particular routes of administration, including, for example, oral or parenteral administration.

Formulations for parenteral administration may contain sterile water or saline, polyalkylene glycols such as polyethylene glycol, oils of vegetable origin, hydrogenated naphthalenes, and the like as common excipients. In particular, biocompatible, biodegradable lactide polymer, lactide/glycolide copolymer, or polyoxethylene-polyoxypropylene copolymers are examples of excipients for controlling the release of the polypeptide in vivo. Other suitable parenteral delivery systems include ethylene-vinyl acetate copolymer particles, osmotic pumps, implantable infusion systems, and liposomes. Formulations for inhalation administration may contain vehicles such as lactose, if desired. Inhalation formulations may be aqueous solutions containing, for example, polyoxyethylene-9-lauryl ether, glycocholate and deoxycholate, or they may be oily solutions for administration in the form of nasal drops. If desired, the compounds can be formulated as gels to be applied intranasally. Formulations for parenteral administration may also include glycocholate for buccal administration For oral administration, tablets or capsules can be prepared by conventional means with pharmaceutically acceptable excipients such as binding agents (e.g., pregelatinized maize starch, PVP, or hydroxypropyl methylcellulose); fillers (e.g., lactose, microcrystalline cellulose or calcium hydrogen phosphate); lubricants (e.g. magnesium stearate, talc or silica); disintegrants (e.g., potato starch or sodium starch glycolate); or wetting agents (e.g., sodium lauryl sulfate). Tablets can be coated by methods known in the art. Preparations for oral administration can also be formulated to give controlled release of the compound.

Nasal preparations can be presented in a liquid form or as a dry product. Nebulised aqueous suspensions or solutions can include carriers or excipients to adjust pH and/or tonicity.

The invention will be further described in the following examples, which do not limit the scope of the invention described in the claims.

EXAMPLES

Materials used in these examples may be obtained from well-known commercial sources. Reported purity is based on weight percent and yield is based on theoretical amount of starting material present in the processes. Analysis of isoflavone levels was performed by well known methods in the art (see, e.g., Song, T et al., *Am J Clin Nutr* 1998 (68 (Suppl)), p. 1474S–9S; Murphy, P A et al. *J. Agric. Food Chem.* 1997 (45), p. 4635–4638; and Wang, H and Murphy, P A; *J. Agric. Food Chem.* 1994 (42), p. 1666–1673.

Example 1

Preparation of an Aqueous Plant Extract

Preparation 1: Aqueous Plant Extract from Soy Germ Flour

Hexane Extraction: A product containing greater than 80% soy germ was ground to yield soy flour. Soy germ products are well known in the art—see, e.g., U.S. Pat. No. 5,952,230 and PCT Publication No. WO 96/10341. Soy germ flour 20 kg was extracted with 53.5 kg of boiling hexane for 5 hours with continuous agitation. The extraction slurry was basket-centrifuged at 50° C. to separate the solids from re-claimed hexane to yield a total of 18.6 kg of defatted soybean meal. This defatted soybean meal was air desolventized at room temperature (21–22° C.) for 24 h.

Ethanol extraction and concentration: The desolventized meal was extracted with 290 kg of ethanol/water (80/20, v/v) at 59–62° C. for 15 hours with continuous agitation. The solids were once again isolated by centrifugation. Centrifugation was carried out at 50° C. to yield approximately 17.4 kg of solids and approximately 350 L of crude aqueous extract. The crude aqueous extract was then vacuum concentrated at 65–70° C. for about 1 h to a volume of approximately 170 L. The vacuum concentration was continued at 65–70° C. for another 4 h, during which a total of 270 L of soft water was gradually added in order to reduce the ethanol level in the extract. No precipitation or color changes were found during the concentration. A final aqueous extract (weighing 48 kg) was obtained with a residual ethanol level of 825 ppm. The extract was approximately 5.5% solids and 0.3–0.35% isoflavones, 0.3–0.5% saponins, 0.2–0.35% oligosaccharides, and 0.38% protein.

Preparation 2: Aqueous Plant Extract from Commercial Soymeal

Commercial low fiber defatted soymeal (250 g) obtained as white flakes was extracted with 80% ethanol/water (2.5 l) for 7 hours at 60° C. The ethanol was evaporated under reduced pressure to yield an aqueous extract (2.0 l) that was 17% solids and 0.2% isoflavones.

Example 2

Isolation of Isoflavones from Aqueous Plant Extracts

The aqueous plant extract from Preparation 1 (100 mL) was adjusted to pH 11.2 using 6 N NaOH. The aqueous phase was then extracted with 1-butanol (100 mL) and the layers separated. The pH of the aqueous phase was adjusted to 6.8 using concentrated HCl and was re-extracted with 1-butanol (60 mL) to yield a second butanol extract. The first butanol extract upon concentration under reduced pressure yielded 1.28 g of yellow solid (3.37% isoflavones), and the second butanol extract upon likewise treatment yielded 0.55 g of pale yellow solid (purity 37.78%, recovery: 56.9%).

In a separate experiment, the aqueous plant extract from Preparation 1 (100 mL) was adjusted to pH 11.8 using 6 N NaOH and extracted with ethyl acetate (100 mL) and the layers separated to yield a first organic extract. The pH of the aqueous phase was adjusted to 6.7 using concentrated HCl and it was extracted with ethyl acetate (100 mL) to yield a second organic extract. The first organic extract upon concentration under reduced pressure yielded 0.4 g of yellow solid (isoflavones purity: 15.71%). The second organic extract upon likewise treatment yielded 0.19 g of pale yellow solid (purity: 67.46%, recovery: 32%).

Example 3

Preparation of Isoflavone Compositions from Organic Plant Extracts by Butanol Addition Through stirring, 1.08 g of an isoflavone sample (produced as described in Example 2) was dissolved in 1000 ml of 94% butanol/water. PEG 200 (0.05 g) was added with continued stirring. The mixture was concentrated through rotary evaporation to a solid, then redissolved in hot water and concentrated to a solid again through rotary evaporation. The same procedure was repeated, independently, with 0.10 g of PEG 200, PEG 400, PEG 600, and PEG 1000.

Example 4

Preparation of Isoflavone Compositions from a Dilute Butanol Process Stream

A 60 mL sample of a butanol process stream containing 1.2% solids was diluted to 720 ml with clean butanol (yielding 0.01% solids). PEG 200 (0.077 g) was added with stirring. The mixture was concentrated to a solid by rotary evaporation, redissolved in water, boiled, and concentrated through rotary evaporation to a solid.

Example 5

Preparation of Isoflavone Compositions from Dried Starting Compositions Using PVP PVP (10% by weight) was added to the dry solids of a dried 45% isoflavone product produced as described in PCT US02/23555; the mixture was dissolved in water. At 5% solids by weight, not all the solids were soluble at 100° C. At 2.5% solids, the material still was not soluble at 100° C. This 2.5% solution was spray dried and a water-soluble material (at 30 mg/100 ml) was produced with a 2.0% by weight residual water content. Spray drying conditions were: feed temperature, 80° C.; inlet air temperature, 160° C.; outlet air temperature, 100° C. The resulting product was a free flowing dry powder with good handling and transport characteristics. A few grams of product were produced in this trial.

Example 6

Preparation of Isoflavone Compositions from Dried Starting Compositions Using PEG PEG (10% by weight) was added to the dry solids of a previously dried 45% isoflavone product (produced as described in PCT US02/23555); the mixture was dissolved in water. At 5% solids by weight, not all the solids were soluble at 100° C. At 2.5% solids, the material was soluble at 100° C. This 2.5% solution was spray dried and a water soluble material (at 30 mg/100 ml) was produced with a 3.4% by weight residual water content. Spray drying conditions were: feed temperature, 80° C.; inlet air temperature, 160° C.; outlet air temperature, 100° C. The resulting product was a powder that appeared sticky. A few grams of product were produced in this trial.

Example 7

Preparation of Isoflavone Compositions from Aqueous Starting Compositions Using PVP PVP of average molecular weight 40,000 was used. 438 g DI water was added to 292 g of an isoflavone concentrate (6% w/w total solids) (produced as described in PCT US02/23555) and mixed at ambient temperature in a 1 L beaker. A total of 1.75 g of PVP 40,000 was added to the concentrate to reach a level of 10% solids. The mixture was transferred to a round-bottom flask and concentrated on a rotovap at 55–60° C., and evaporation was stopped when the butanol reading on a hydrometer read 6% alcohol. The concentrate was spray dried on a lab scale Buchii 190 (Brinkmann Instruments, Mississauga, ON) spray dryer with the following parameters: inlet air temperature, 160° C.; outlet air temperature, 100° C., airflow 500, aspirator 10. Approximately 100 mL of feed produced 5.2 g of powdered isoflavone at 1.56% w/w moisture content. The material dried nicely, with no sticking to the walls or outlet of the spray dryer. The resulting product was a free flowing dry powder with good handling and transport characteristics. The product was soluble at 30 mg/100 ml at ambient temperatures.

Example 8

Production of an Isoflavone Composition Using PVP

PVP of average molecular weight 40,000 was used. The starting composition was a suspension of 4.64% by weight of solids (45% isoflavones) in a water-saturated butanol solution. 10% by weight of the dry solids was added in the form of PVP and mixed in an unbaffled opaque tank. No visible inspection was made to ensure that the mixture was solubilized. The suspension was placed in a one stage flash vessel at 62° C. (+/−2° C.) and 20 in. of vacuum. Water was periodically added to the mixture until a suspension containing 3% by weight butanol and 4.3% by weight dry solids was achieved. The suspension was spray dried under the following conditions: feed temperature, 80° C., inlet air temperature, 160° C.; outlet air temperature, 100° C. The material dried nicely, with no sticking to the walls or outlet of the spray dryer. The resulting product was a free flowing dry powder with good handling and transport characteristics. The spray-dried product contained 10 ppm residual butanol. The product was not completely soluble at 30 mg/100 ml at ambient temperatures. The solution was slowly heated and when the temperature reached 52° C., the material became water-soluble. This solution was slowly cooled back to ambient temperature and the material remained in solution. Approximately 3.4 kg of spray-dried product was produced in this trial.

Example 9

Transmittance of Isoflavone Compositions

Isoflavone composition samples produced by the methods of Examples 3–8 were prepared at a concentration of 30–32 mg of product in 100 g of water and placed in a spectrophotometer cell, and the % transmittance recorded at 400, 500, 600, and 700 nm. Samples were compared to commercially available isoflavone products from Central Soya, Solbar, and ADM (Novasoy®) and to product produced according to PCT US02/23555. The results are presented in Table 1. Transmittance at 500 nm for product produced according to PCT US02/23555 typically ranged from 81 to 89%.

TABLE 1

| Sample | 400 nm | 500 nm | 600 nm | 700 nm |
| --- | --- | --- | --- | --- |
| Water | 100.09 | 100.02 | 100.02 | 99.61 |
| Central Soya Prevastein-HC | 55.35 | 59.87 | 63.07 | 65.63 |
| Solbar | 43.39 | 56.23 | 63.34 | 68.36 |
| ADM Novasoy ® | 41.21 | 60.38 | 65.37 | 68.36 |
| Product produced according to PCT US02/23555 | 53.75 | 81.56 | 86.48 | 89.84 |

TABLE 1-continued

| Sample | 400 nm | 500 nm | 600 nm | 700 nm |
|---|---|---|---|---|
| Product produced according to PCT US02/23555 | 86.24 | 88.55 | 90.93 | 92.58 |
| Product from Example 3 | 83.55 | 91.87 | 94.41 | 96.09 |
| Product from Example 7 (10% PVP, spray dried) | 83.51 | 91.52 | 94.54 | 96.48 |
| Product from Example 5 (10% PVP 10,000) | 86.57 | 93.93 | 96.02 | 97.27 |
| Product from Example 5 (10% PVP 55,000, POS Trial) | 88.38 | 96.32 | 98.1 | 99.22 |
| Product from Example 6 (PEG 200, 5% solids) | 81.6 | 91.62 | 94.95 | 96.88 |
| Product from Example 6 (PEG 200, 2.5% solids) | 87.21 | 95.6 | 97.75 | 98.83 |

As can be seen from Table 1, the isoflavone compositions of the present invention exhibit transmittance values of greater than 75% at all wavelengths tested. Compositions of the invention also exhibit a % transmittance at 500, 600, and 700 nm that is greater than the % transmittance at 500, 600, and 700 nm of other isoflavone compositions that do not contain a hydrophilic polymer.

Example 10

Production of Juice Beverages

Cranberry juice concentrate (20.38 g) was mixed with 0.41 g of PVP of average molecular weight 10,000 then diluted with 50 mL of water and sonicated for 10 minutes. The mixture was centrifuged and the supernatant decanted. The precipitate was dried at 60° C. and found to have a mass of 2.75 g. Approximately 0.01% by weight on an isoflavone composition (prepared as described above) was added to the supernatant and transmittance was assessed at 600 nm. Transmittance of the juice beverage was 97.15%. In contrast, when 0.01% by weight of the same isoflavone composition was added to untreated cranberry juice concentrate, transmittance at 600 nm was 57.85%.

In another experiment, 0.10 g of PVP of average molecular weight 10,000 was added to 20.15 g of cranberry juice concentrate. The mixture was diluted with 50 mL of water, sonicated for 10 minutes, and then centrifuged. The supernatant was decanted and the precipitate was dried at 60° C. (mass of 1.38 g). Approximately 0.01% by weight on an isoflavone composition (prepared as described above) was added to the supernatant and transmittance was assessed at 600 nm. Transmittance of the juice beverage was 97.84%. In contrast, when an isoflavone composition was added to untreated cranberry juice concentrate, transmittance at 600 nm was 57.85%.

Similar experiments were performed with apple and grape juice concentrates. Approximately 0.225 g of PVP of average molecular weight 10,000 was added to 50 mL of apple juice concentrate (42° Brix) or grape juice concentrate (45° Brix) with stirring. The mixtures were centrifuged and the supernatants decanted. The precipitates were dried at 65° C. and found to have a mass of 1.773 g for the apple juice concentrate and 0.75 g for the grape juice concentrate. Approximately 0.01% by weight on an isoflavone composition (prepared as described above) was added to each supernatant and transmittance was assessed at 600 nm. Transmittance of the apple and grape juice beverages was 63.77% and 66.74%, respectively (see Table 2). In contrast, when an isoflavone composition was added to untreated apple or grape juice concentrates, transmittance at 600 nm was 56.42% and 38.78%, respectively (see Table 2).

TABLE 2

| Wavelength (nm) | H2O STD | Treated Grape & Isoflavone | Untreated grape & Isoflavone | Treated Apple & Isoflavone | Untreated apple & Isoflavone |
|---|---|---|---|---|---|
| 600 | 100.08 | 66.74 | 38.78 | 63.77 | 56.42 |

Color of the juice beverages was determined using the following procedure on a dual beam, xenon flash Color Quest XE spectrophotomer by HunterLab (Reston, Va.). The color is characterized by three distinct values, the L-value, a-value and b-value. The L-value corresponds to brightness, with a higher value corresponding to a brighter product. The a-value assesses the red/green coloration with positive and negative values corresponding to the degree of red and green, respectively. Similarly, the b-value quantifies the degree of yellow/blue coloration with positive values relating to yellow hues and negative values to blue. Mode type of the spectrophotomer was set to "Reflectance, Specular Exclusion (RSEX)," area view was set to "small," and port size was set to "0.375 inches, then the software standardization procedures were followed for "white tile for calibration." For each beverage, the 20-mm transmission cell was filled to slightly more than half the height of the cell such that the reflectance port was completely covered. The base of the cell was tapped to ensure homogeneity. The transmission cell was placed in front of the reflectance port, covered with the light trap, and the instrument run to characterize sample color.

The color of the juice beverages is presented in Table 3. The treated juice beverages were brighter, as indicated by the higher L-values. The treated grape and apple beverages had less red coloration (lower a-values) and less of a yellow hue (lower b-values) than the untreated apple and grape juice beverages. Treated cranberry juice beverages had more red coloration (higher a-value) and less of a yellow hue (lower b-value) than untreated cranberry juice beverages.

TABLE 3

| Sample | L* | A* | b* |
|---|---|---|---|
| H2O STD | 100.02 | 0 | −0.01 |
| Grape Treated | 77.66 | 10.78 | 23.66 |
| Grape Untreated | 58.49 | 18.28 | 27.29 |
| Apple Treated | 79.47 | 1.93 | 24.76 |
| Apple Untreated | 74.41 | 3.46 | 30.37 |
| Untreated CJC plus isoflavone | 72.28 | 12.97 | 24.02 |
| Treated CJC plus isoflavone | 88.79 | 24.12 | 3.27 |

A* red-green, (+)more red;
b* yellow-blue, (+)more yellow;
L* lightness,
100 = clear

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of making a juice beverage, said method comprising
    a) combining a fruit juice with 0.15 to 3% by weight of polyvinyl pyrrolidone (PVP) or polyvinyl polypyrrolidone (PVPP) to form a precipitate containing polyphenolic compounds;
    b) removing said precipitate from said fruit juice; and
    c) adding at least 0.01% by weight of an isoflavone composition to said fruit juice to produce said beverage, said isoflavone composition comprising:
        i) two or more isoflavones, wherein said isoflavones represent about 15% to about 70% by weight of the composition; and
        ii) about 0.5% to about 30%, by weight, of a hydrophilic polymer, wherein said isoflavone composition, upon preparation of a mixture of about 0.03% by weight of the composition in water, exhibits a transmittance at 500 nm of at least 75%,
    wherein said beverage exhibits a transmittance at 600 nm that is increased at least 15% relative to the transmittance of a corresponding beverage prepared without removing said polyphenolic compounds.

2. The method of claim 1, wherein removing said precipitate comprises filtration or centrifugation.

3. The method of claim 1, wherein said fruit juice is an apple, cranberry, orange, or grape juice concentrate.

4. The method of claim 1, wherein said increased transmittance of said beverage is maintained upon storage of said beverage for at least 30 days at a temperature ranging from about 4° C. to about 25° C.

5. The method of claim 1, wherein said beverage exhibits a transmittance at 600 nm that is increased at least 30% relative to the transmittance of a corresponding beverage prepared without removing said polyphenolic compounds.

6. The method of claim 1, wherein said beverage exhibits a transmittance at 600 nm that is increased at least 50% relative to the transmittance of a corresponding beverage prepared without removing said polyphenolic compounds.

7. The method of claim 1, wherein said hydrophilic polymer is selected from the group consisting of PVP, PVPP, polyvinyl formyl, polyvinyl alcohol, polypropylene glycol, polyvinyl caprolactam, polyethylene oxide, polyethylene glycol, and polyvinyl N-methyl pyrrolidone.

8. The method of claim 1, wherein said hydrophilic polymer is PVP.

9. The method of claim 1, wherein said transmittance of said composition is at least 85%.

10. The method of claim 1, wherein said transmittance of said composition is at least 95%.

11. The method of claim 1, wherein said isoflavones represent about 25% to about 65% by weight of the composition.

12. The method of claim 1, wherein said isoflavones represent about 35% to about 55% by weight of the composition.

13. A method of making a juice beverage, said method comprising
    a) combining a fruit juice with 0.15 to 3% by weight of PVP and at least 0.01% by weight of an isoflavone composition to form a precipitate containing polyphenolic compounds endogenous to said fruit juice, said isoflavone composition comprising:
        i) two or more isoflavones, wherein said isoflavones represent about 15% to about 70% by weight of the composition; and
        ii) about 0.5% to about 30%, by weight, of a hydrophilic polymer, wherein said isoflavone composition, upon preparation of a mixture of about 0.03% by weight of the composition in water, exhibits a transmittance at 500 nm of at least 75%; and
    b) removing said precipitate from said fruit juice to produce said fruit beverage, wherein said beverage exhibits a transmittance at 600 nm that is increased at least 15% relative to the transmittance of a corresponding beverage prepared without removing the polyphenolic compounds endogenous to said fruit juice.

14. A method of making an isoflavone composition, said method comprising
    a) providing an organic plant extract containing two or more isoflavones and at least one organic solvent;
    b) combining said organic plant extract with about 0.5% to about 30% by weight of a hydrophilic polymer to produce a combined extract;
    c) replacing said at least one organic solvent in said combined extract with an aqueous solution to produce an aqueous extract; and
    d) concentrating said aqueous extract to produce said isoflavone composition, wherein: said isoflavone composition contains two or more isoflavones, said isoflavones representing about 15% to about 70% by weight of said isoflavone composition, and said isoflavone composition, upon preparation of a mixture of about 0.03% by weight of said isoflavone composition in water, exhibits a transmittance at 500 nm of at least 75%.

15. A method of making an isoflavone composition, said method comprising:
    a) providing a starting composition comprising two or more isoflavones;
    b) combining said starting composition with a hydrophilic polymer to produce an isoflavone-polymer mixture, wherein either said starting composition or said hydrophilic polymer is an aqueous solution, and wherein the final concentration, by weight, of said hydrophilic polymer in said isoflavone-polymer mixture is from about 0.5% to about 30%; and
    c) heating said isoflavone-polymer mixture; and
    d) concentrating said isoflavone-polymer mixture to produce said isoflavone composition, wherein: said isoflavone composition contains two or more isoflavones, said isoflavones representing about 15% to about 70% by weight of the composition, and said isoflavone composition, upon preparation of a mixture of about 0.03% by weight of said isoflavone composition in water, exhibits a transmittance at 500 nm of at least 75%.

16. A method of making an isoflavone composition, said method comprising:
    a) providing a starting composition comprising two or more isoflavones;
    b) combining said starting composition with a hydrophilic polymer to produce an isoflavone-polymer mixture;
    c) suspending said isoflavone-polymer mixture in an aqueous solution to result in a final concentration of about 0.5% to about 30% by weight of the hydrophilic polymer;
    d) heating said aqueous isoflavone-polymer mixture; and
    e) concentrating said aqueous isoflavone-polymer mixture to produce said isoflavone composition, wherein: said isoflavone composition contains two or more isoflavones, said isoflavones representing about 15% to about 70% by weight of said isoflavone composition, and said isoflavone composition, upon preparation of a mixture of about 0.03% by weight of said isoflavone composition in water, exhibits a transmittance at 500 nm of at least 75%.

* * * * *